United States Patent [19]
Ro

[11] Patent Number: 5,782,850
[45] Date of Patent: Jul. 21, 1998

[54] METHOD FOR TREATING TRIGGER FINGER, AND MEDICAL INSTRUMENT THEREFOR

[76] Inventor: Man Tack Ro, 326-101, Olympic Apartment, 89, Pang I Dong, Song Pa Ku, Seoul, Rep. of Korea

[21] Appl. No.: 777,116

[22] Filed: Dec. 30, 1996

Related U.S. Application Data

[63] Continuation of Ser. No. 510,932, Aug. 3, 1995, abandoned.

[30] Foreign Application Priority Data

Oct. 12, 1994 [KR] Rep. of Korea ............... 1994-26069
Jun. 14, 1995 [KR] Rep. of Korea ............... 1994-15681

[51] Int. Cl.⁶ ............................................. A61B 17/32
[52] U.S. Cl. ..................... 606/167; 606/170; 606/159
[58] Field of Search ........................... 606/167, 170, 606/159, 95, 99; 604/116, 164, 272; 128/749, 754, 172, 174, 176

[56] References Cited

U.S. PATENT DOCUMENTS 2,649,860  4/1953  Royer ............................ 606/167
4,382,444  5/1983  Malmin ......................... 606/187
5,029,573  7/1991  Chow ............................. 606/167
5,222,977  6/1993  Esser ............................ 606/222
5,353,804  10/1994  Kornberg et al. ............ 128/754
5,397,333  3/1995  Knoepfler ..................... 606/167
5,569,283  10/1996  Green et al. ................. 606/167

FOREIGN PATENT DOCUMENTS

552980-A1  7/1993  European Pat. Off. ...... 606/167
3416-490-C  2/1986  Germany ..................... 606/167
1389-766-A  4/1988  U.S.S.R. ..................... 606/167

Primary Examiner—Gary Jackson
Assistant Examiner—Daphna Shai
Attorney, Agent, or Firm—McDermott, Will & Emery

[57] ABSTRACT

A medical instrument for treating trigger finger which has an operation portion having a forwardly pointed first tip at a front end, a second tip directed rearwardly of the first tip, and a transverse groovelike depression with a hook-shaped edge extended downwardly and forwardly from the second tip. A grip portion is attached to the operation portion.

6 Claims, 7 Drawing Sheets

METHOD FOR TREATING TRIGGER FINGER, AND MEDICAL INSTRUMENT THEREFOR

This application is a continuation of application Ser. No. 08/510,932 filed Aug. 3, 1995 now abandoned.

FIELD OF THE INVENTION

The present invention relates to a method for treating a condition known as "trigger finger" which is a painful symptom causing pain when a finger extends or flexes actively or passively, and more particularly to a method for treating trigger finger, by which the trigger finger is treated without the skin being incised, and a medical instrument therefor.

BACKGROUND OF THE RELATED ART

There are two techniques to treat the trigger finger: one is performed with the skin being incised, and the other without the skin being incised. According to the conventional way to treat the trigger finger with the skin being incised, the skin must be sutured typically after the operation, the suture being removed in 10–14 days. In order to avoid this, an alternative way was developed to treat the trigger finger without the skin being incised.

In this technique, with the affected finger flexed, the tip of an injector needle is inserted until the pulley, with the slope of the needle being parallel with the vertical axis of a flexor tendon, and the finger extends when the tip of the needle reaches the pulley, which is thus incised (see Vol. 24, No. 1, The Journal of the Korean Orthopedic Association.

This method is advantageous in not incising the skin. However, extending the finger must be repeated several times in order to incise all the corresponding pulleys. In addition, the needle is supposed to be suitable for prickling the skin, not for incising pulleys. For this reason, incising the skin is not easy to perform. Furthermore, this method may create damage on the peripheral tendon tissues.

For another way, there was suggested a method in which the skin on an attacked portion is incised and then corresponding pulleys surrounding the flexor tendon are cut using an instrument like a knife (See The Journal of Bone and Joint Surgery Vol. 74-B, No. 3). One example of performing this method will be discussed schematically with reference to FIGS. 14–17.

Figure 14:
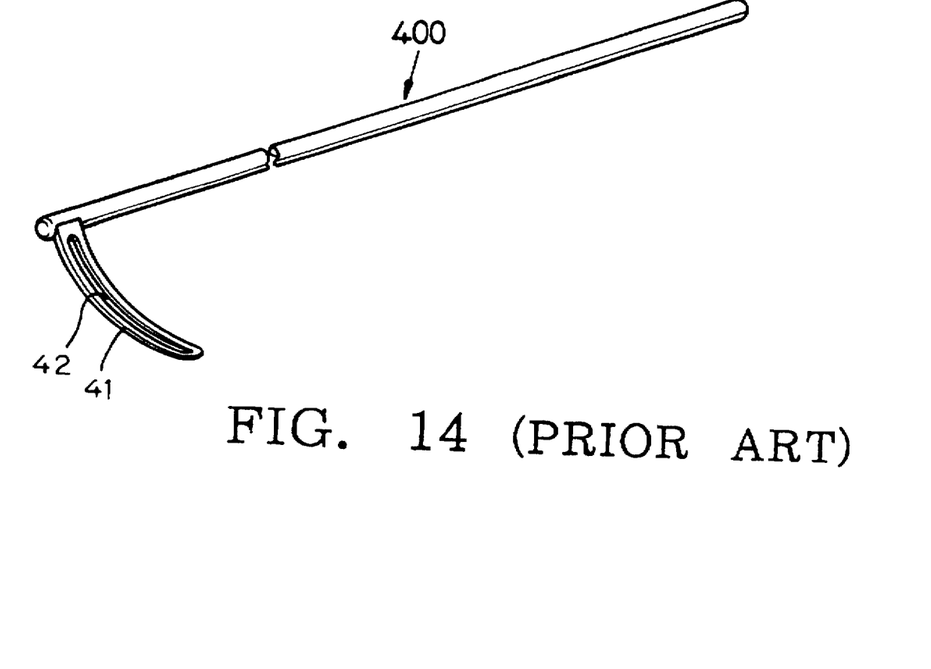
FIG. 14 is a perspective view of a conventional pulley hook.
Figure 15:
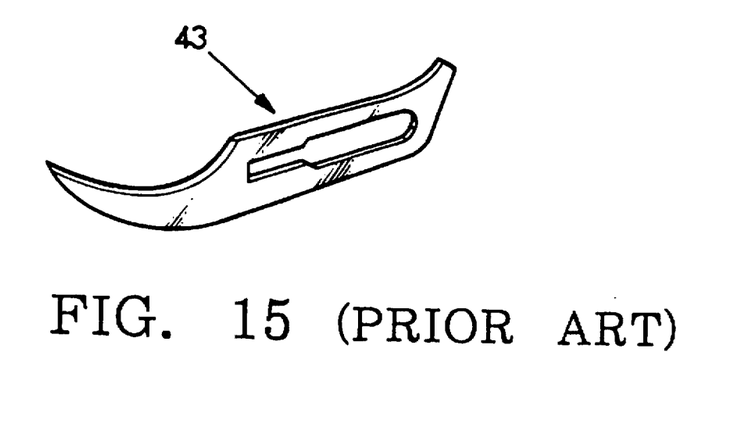
FIG. 15 is a perspective view of a knife used together with the conventional pulley hook.

Conventional instruments used in treatment of the trigger finger typically include a pulley hook 400 formed in such a manner that an aneurysm needle is bent and a slot 42 is formed along the bent portion, and a curved knife 43 to be inserted into slot 42.

Figure 16:
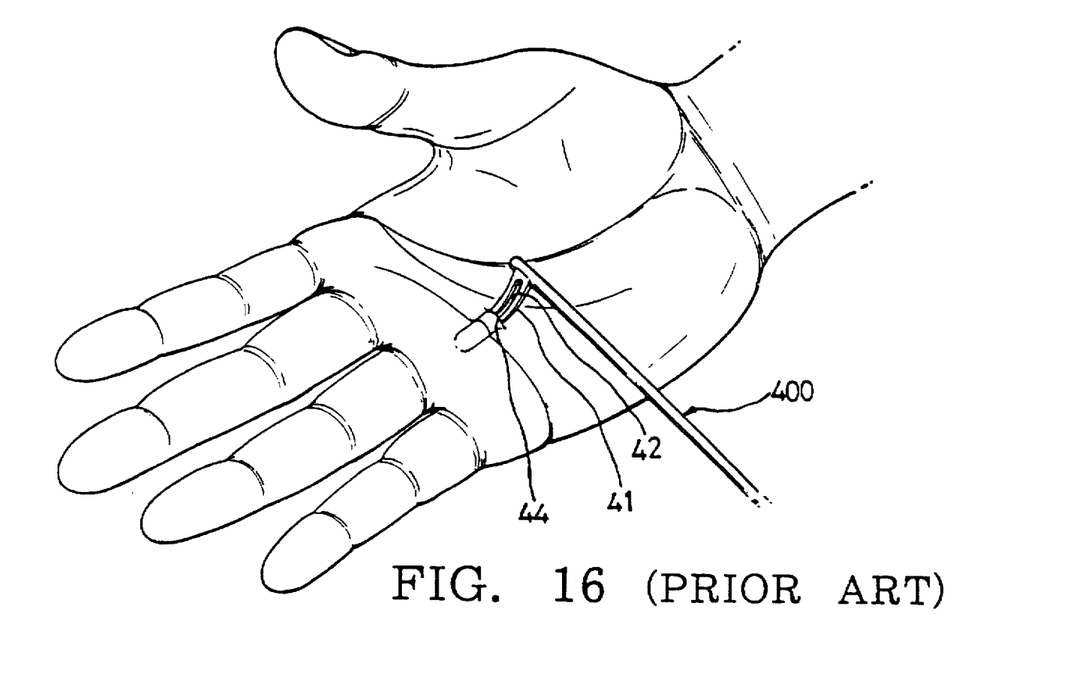
FIG. 16 is a perspective view in which an operation is performed with the conventional pulley hook.
Figure 17:
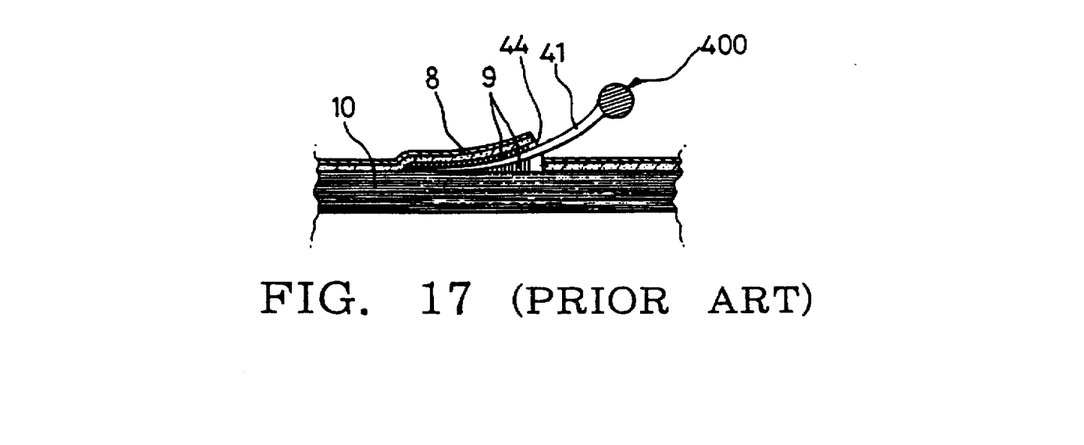
FIG. 17 is a partial sectional view of FIG. 16.

In order to handle the trigger finger using these instruments, the skin is cut around the attacked portion, the tip of pulley hook 400 is inserted between pulley 9 and flexor tendon 10 through the cut portion 44, and knife 43 is put into slot 42 of pulley hook 400. By doing so, pulley 9 is incised. Thereafter, knife 43 and hook 400 are removed and then cut portion 44 of the skin is treated.

As stated above, in order to treat the trigger finger according to those methods, the skin must be cut, thus involving inconvenience and severe pain to the patient. Further, when those methods are employed, it may take a long time for the operated finger to be healed enough to be used normally, and there may be complications.

SUMMARY OF THE INVENTION

Therefore, in order to overcome or improve such problems or drawbacks, there are provided a medical instrument and a method for treating trigger finger which is easily treated even by a unfamiliar doctor, without the skin being incised and the flexor tendon being damaged.

To accomplish the object of the present invention, there is provided a medical instrument for trigger finger which comprises: an operation portion, the operation portion having a front end with a first tip pointed forwardly at the front end, a second tip directed pointed rearwardly relative to the first tip, and a groovelike transverse depression with a hook-shaped cutting edge extended downwardly and forwardly from the second tip; and a grip portion.

In another aspect of the present invention, there is further provided a method for treating trigger finger comprising the steps of: inserting a medical instrument, comprising an operation portion having a front end with a first tip pointed forwardly and a second tip pointed rearwardly of the first tip, with a groovelike transverse depression, with a hook-shaped cutting edge extended downwardly and forwardly from the second tip, and a grip portion, into the finger at a location corresponding to an affected portion thereof until the second tip reaches an end of the pulley between the skin and the pulley or between the pulley and a flexor tendon; and pulling out said instrument in a direction opposite a direction of the insertion.

DETAILED DESCRIPTION OF THE PREFERRED EMBODIMENTS

Preferred embodiments of the present invention will now be described with reference to the attached drawings.

Figure 1:
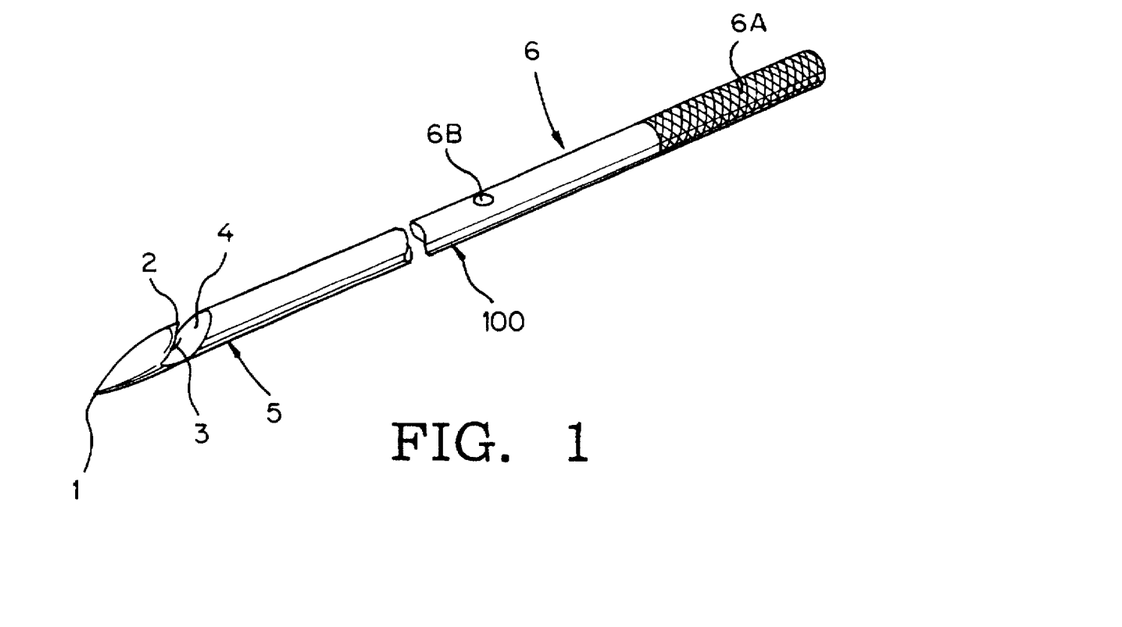
FIG. 1 is a perspective view of a first embodiment of a medical instrument of the present invention.
Figure 2:
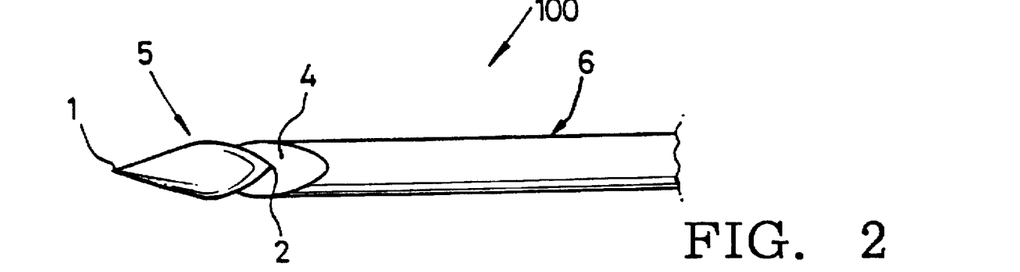
FIG. 2 is a front view of the head of the present invention of FIG. 1.
Figure 3:
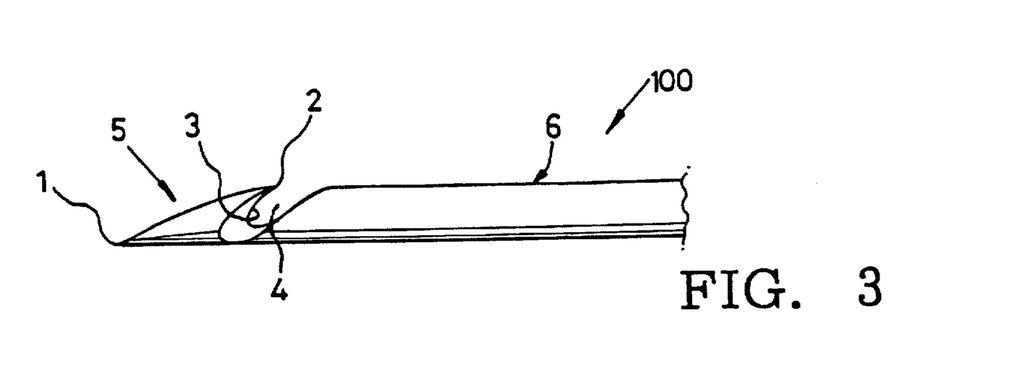
FIG. 3 is a plan view of the head of the present invention of FIG. 1.

As best seen in FIGS. 1–3, a trigger finger treating instrument 100 of the present invention is made with a rod of stainless steel. The front part thereof is an operation portion 5, and the rear part a grip portion 6.

Operation portion 5 has a pointed first tip 1 at the front end, a second tip 2 pointed rearwardly from the first tip 1, and a transverse groovelike recess 4 with a hook shaped edge 3 extended downwardly and forwardly from the second tip 2. In other words, the front portion is made with first tip 1, and the edge 3 is hook-shaped at the back of first tip 1. At the grip portion 6, an indicator 6B used to detect the position of second tip 2 around the circumference.

In order to facilitate gripping of trigger finger treating instrument 100, an uneven portion 6A is formed on the surface of grip portion 6, or a grip-mounting configuration is provided at a predetermined position of grip portion 6 so that an additional grip member (not shown) is mounted to grip portion 6. Alternatively, grip portion 6 may be formed in a structure of tongs.

A method of treating trigger finger using the instrument 100 of the present invention is described below.

Figure 4:
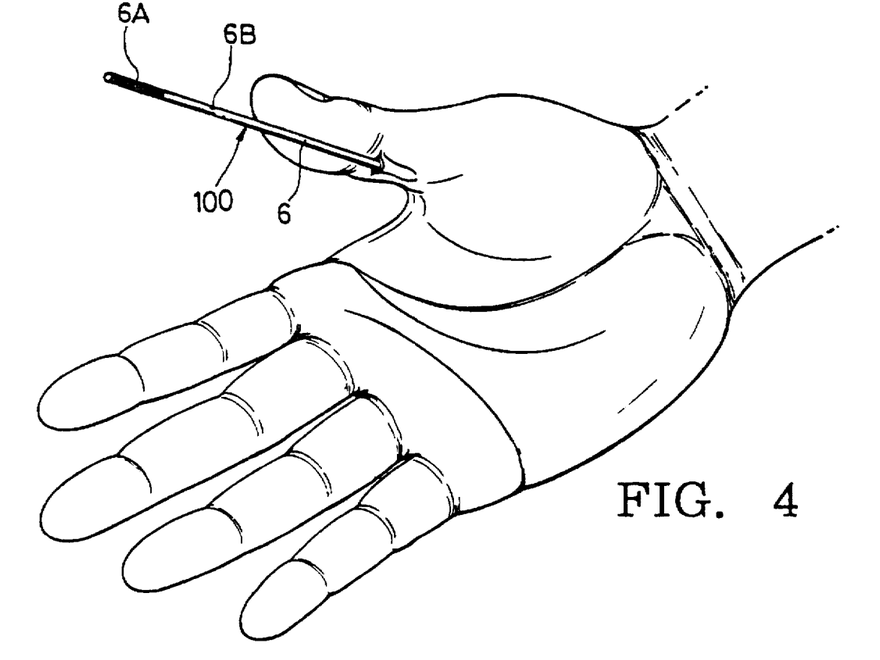
FIG. 4 is a perspective view showing a state in which an operation is performed with the instrument of FIG. 1.
Figure 5:
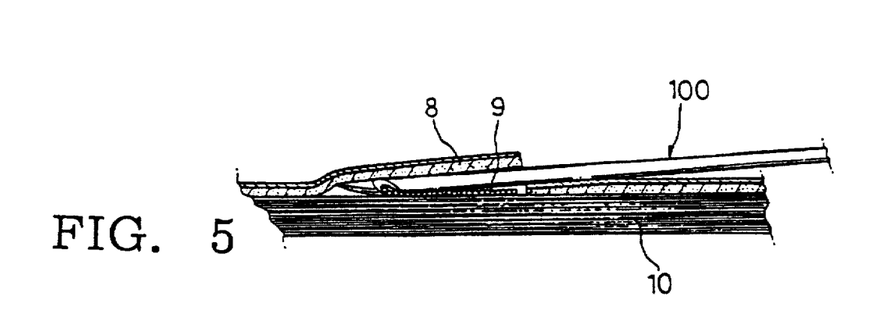
FIG. 5 is a partial sectional view of the state shown in FIG. 4.
Figure 6:
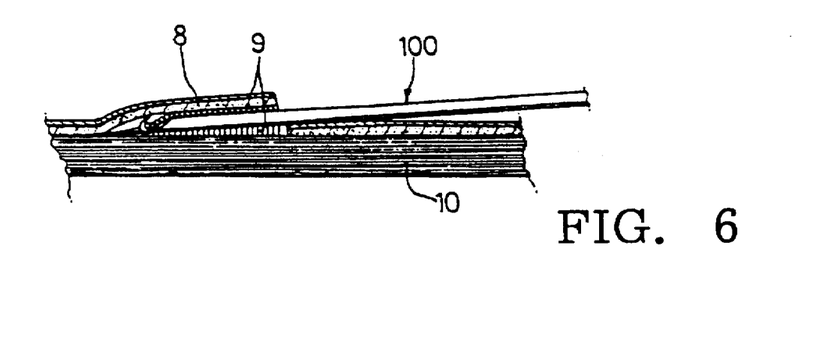
FIG. 6 is another partial sectional view of the state of FIG. 4.

As shown in FIGS. 4, 5 and 6, first tip 1 is inserted into skin 8 after being placed in correspondence with the front portion of pulley 9 of the affected portion of the finger to be treated, and put until second tip 2 reaches the end of pulley 9 which is to be incised, between skin 8 and pulley 9 or between pulley 9 and flexor tendon 10.

Thereafter, instrument 100 is rotated so that second tip 2 engages with the back end of pulley 9 to be incised. Instrument 100 is moved up and down so that the portion of the pulley 9 to be cut is located in depression 4.

After pulley 9 is placed in depression 4 and its back end comes into contact with the edge 3, instrument 100 is pulled forward slightly. Then, when this state is confirmed, instrument 100 is pulled in a direction that is the reverse of the direction of the insertion so that pulley 9 is cut by the edge 3 and instrument 100 exits skin 8. Here, whether pulley 9 is cut completely or not can be confirmed by flexing the finger. In FIG. 4, there is shown a case that instrument 100 performs an operation from the finger to the wrist. However, it is also possible to perform an operation from the wrist to the finger.

Referring to FIGS. 7–11, trigger finger treating instrument 200 is processed with a stainless steel strip. The front portion is an operation part 15, and the rear portion is a coupling part 16. Operation portion 15 has a pointed first tip 11 pointing forwardly at the front end, a second tip 12 directed rearwardly relative to the first tip 11, and a transverse groovelike depression 14 with a hook-shaped edge 13 extended downwardly and forwardly from the second tip 12. In other words, the front portion is made with first tip 11, and the edge 13 is hook-shaped at the back of first tip 11. A coupling slot 17 is formed in coupling part 16 extended from operation portion 15 so as to be connected to the coupling member of grip 50 mounting the conventional surgical knife. Instrument 200 is used while coupled to conventional grip 50 (see FIG. 8).

A method of treating trigger finger using the instrument 200 of the present invention will be described below.

Figures 9, 10:
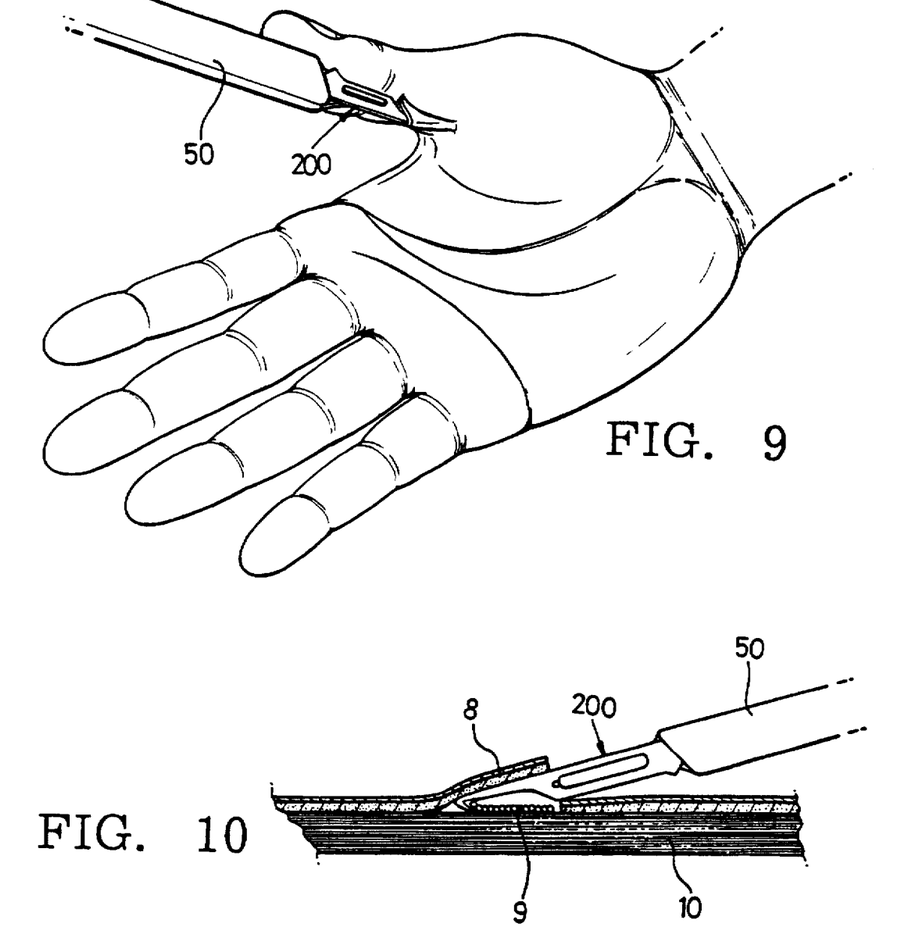
FIG. 9 is a perspective view in which an operation is performed with the instrument of FIG. 7.
FIG. 10 is a partial sectional view of the state shown in FIG. 7.
Figure 11:
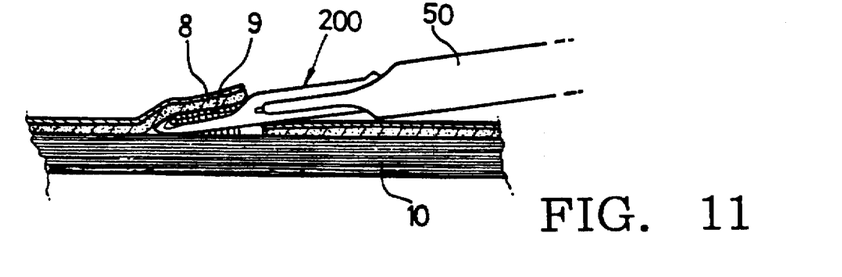
FIG. 11 is another partial sectional view of the state of FIG. 7.

As shown in FIGS. 9, 10 and 11, first tip 11 is inserted into skin 8 placed corresponding to the front portion of pulley 9 of the attacked portion, and put until second tip 12 reaches the end of pulley 9 which is to be incised, between skin 8 and pulley 9 or between pulley 9 and flexor tendon 10.

Thereafter, instrument 200 is rotated so that second tip 12 engages with the back end of pulley 9 which is to be incised. Instrument 200 is moved up and down so that the portion of pulley 9 which is to be cut is located in depression 14.

After pulley 9 is located in depression 14 and its back end comes into contact with edge 13, instrument 200 is pulled forward slightly. Then, when this state is confirmed, instrument 200 is pulled in the reverse direction of the insertion so that pulley 9 is cut by edge 13 and instrument 200 gets out of skin 8. Here, whether pulley 9 is cut completely or not can be confirmed by flexing the finger. In FIG. 9, there is shown a case that instrument 200 performs an operation from the finger to the wrist. However, it is also possible to perform an operation from the wrist to the finger.

Figure 7:
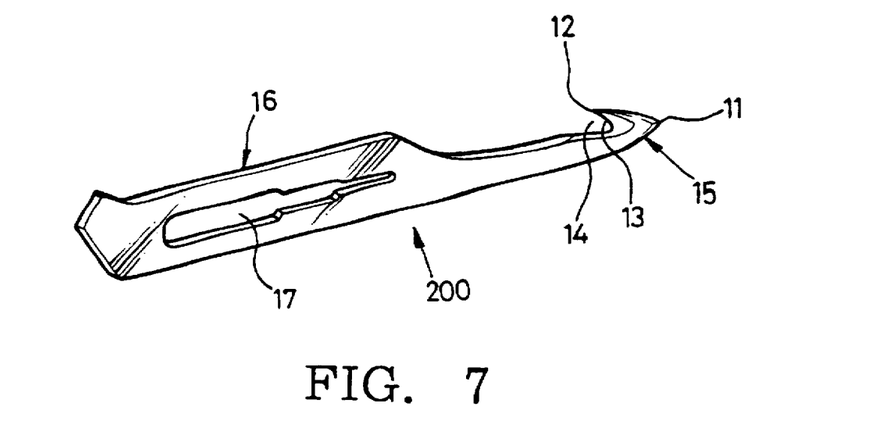
FIG. 7 is a perspective view of a second embodiment of the medical instrument of the present invention.
Figure 8:
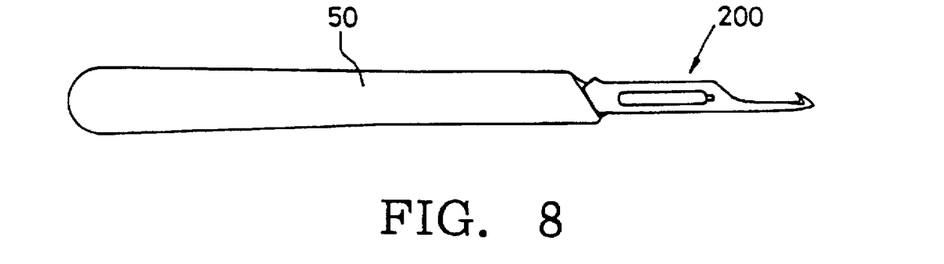
FIG. 8 is a side view in which a grip member is joined to the instrument of FIG. 7.
Figure 12:
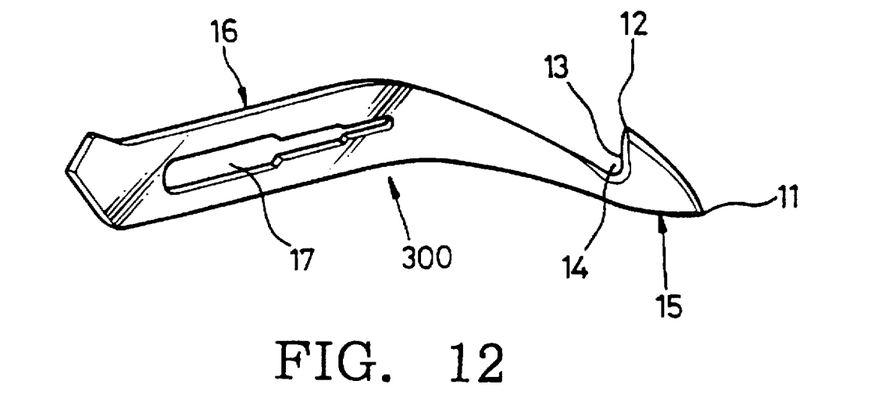
FIG. 12 is a perspective view of a third embodiment of the medical instrument of the present invention.
Figure 13:
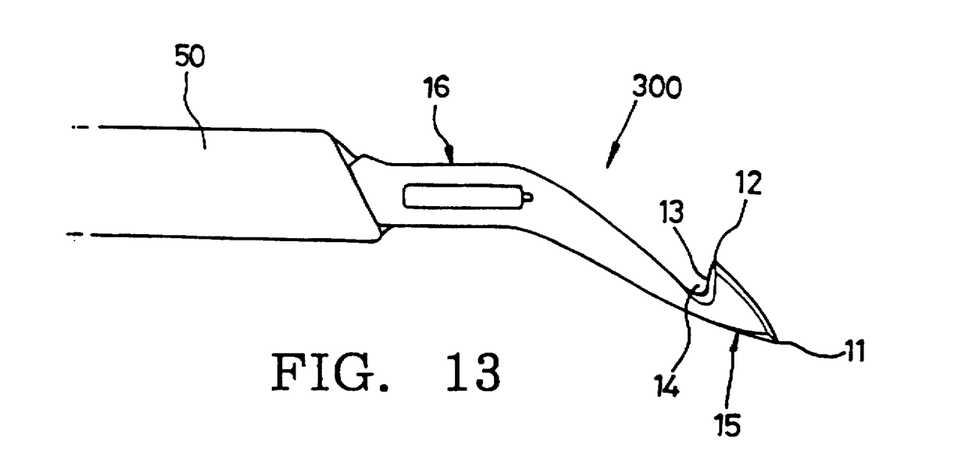
FIG. 13 is a side view in which a grip member is fixed to the instrument of FIG. 12.

As shown in FIG. 12, for still another modification of the present invention, there is presented an instrument 300 in which operation portion 15 of instrument 200 of FIG. 7 is bent outward from coupling portion 16 i.e., at an outward angle relative to a longitudinal direction of the coupling portion. In this case, except that operation portion 15 is bent from coupling portion 16, other features are the same as those of FIG. 7. An advantage of this embodiment is that, when instrument 300 is inserted between skin 8 and pulley 9 in the same manner as that shown in FIGS. 5 and 10, the distance between the grip thereof and the body is widened. This broadens the range of action, facilitating operation.

As described above, in case that the pulley is cut to treat the trigger finger using the instruments of the present invention, there is no need for incising the skin. This facilitates the treatment of the trigger finger, with the patient's pain being significantly reduced. In addition, the present invention eliminates complications which may be caused due to skin incision. Although the present invention has been described and illustrated in detail, it should be clearly understood that the same is by way of illustration and example only and is not to be taken by way of limitation, the spirit and scope of the present invention being limited only by the terms of the appended claims.

What is claimed is:

1. A medical instrument for treating a trigger finger, comprising:

an operation portion consisting of a tapered cord pointed front end with a first tip pointed forwardly at the front end, a second pointed tip pointed rearwardly relative to the first tip, and a groovelike transverse depression with a hook-shaped cutting edge extended downwardly and forwardly and along the entire length of the second tip; and a grip portion.

2. The medical instrument according to claim 1, wherein:

said operation portion comprises a coupling portion with an elongate longitudinal coupling slot at a rear part of said coupling portion.

3. The medical instrument according to claim 1, wherein:

said operation portion is bent away from a longitudinal direction of said coupling portion.

4. The medical instrument according to claim 1, wherein said operation portion has an essentially circular cross section and the grip portion is unitarily formed with said operation portion and has an essentially circular cross section.

5. A method for treating a trigger finger by cutting a pulley under the skin thereof, comprising the steps of:

inserting only an operation portion of a medical instrument comprising a grip portion and an operation portion consisting of a front end with a first tip pointed forwardly and a second pointed tip pointed rearwardly of the first tip, with a groovelike transverse depression with a hook-shaped cutting edge extended downwardly and forwardly and along an entire length of the second tip, into the finger at a location corresponding to an affected portion thereof until the second tip reaches an end of the pulley between the skin and the pulley or between the pulley and a flexor tendon; and pulling out said instrument in a direction opposite a direction of the insertion.

6. The method according to claim 5, comprising the further steps of:

rotating said instrument after the inserting step, so that the end of the pulley engages with said second tip portion; and moving said instrument so that the pulley is positioned within the depression to be hooked and cut by the hook-shaped cutting edge.

* * * * *